United States Patent [19]
Marton

[11] Patent Number: 5,965,896
[45] Date of Patent: Oct. 12, 1999

[54] APPARATUS AND METHOD FOR SCRATCH WEAR TESTING OF THIN FILMS

[75] Inventor: Denes Marton, Houston, Tex.

[73] Assignee: Marton & Associates, Inc., Houston, Tex.

[21] Appl. No.: 09/030,334

[22] Filed: Feb. 25, 1998

Related U.S. Application Data

[60] Provisional application No. 60/038,979, Feb. 26, 1997.

[51] Int. Cl.$^6$ .................................................. G01N 21/86
[52] U.S. Cl. .............................. 250/559.4; 250/559.22; 356/237.2
[58] Field of Search ........................... 250/559.4, 559.22, 250/559.45, 306, 307; 356/237.2

[56] References Cited

U.S. PATENT DOCUMENTS

| 4,954,722 | 9/1990 | Fine et al. ................................. 250/216 |
| 5,712,701 | 1/1998 | Clementi et al. ..................... 356/237.2 |

OTHER PUBLICATIONS

R. Kaneko et al: "Recent Progress in Microtribology," Wear, vol. 200, (1996), pp. 296–304. (Month Unknown).

J.B. Pethica: "Mircohardness Tests with Penetration Depths Less than Ion Implanted Layer Thickness," V. Ashford et al (eds.) Icon Implantation Into Metals, Pergamon Press, Oxford, (1982), p. 147–156. (Month Unknown).

ASTM G 99–95A, Annual Book of ASTM Standards, vol. 03.02, (1997), pp. 392–396. (Month Unknown).

S. Bennett et al: "Multifunction Scratch Tester," Surface & Coatings Technology, vol. 75, (1995), pp. 869–876. (Month Unknown).

K. Holmberg et al: "Coatings Tribology," Elsevier, Amsterdam, (1994), pp. 209–308. (Month Unknown).

J. Lorincik et al: "Scanning Scattering Microscope for Surface Microtopography and Defect Imaging," Journal of Vacumm Science and Technolgy B, vol. 14 (1996), pp. 2417–2433. Apr. 1996.

Bjuggren et al: "Quality Assessment of Engineering Surfaces by Infrared Scattering," Proc. Of SPIE, vol. 2536, (1995), pp. 327–336. (Month Unknown)

*Primary Examiner*—Que T. Le
*Attorney, Agent, or Firm*—Browning Bushman

[57] ABSTRACT

Methods and apparatus are provided for generating scratch wear resistance information on a given specimen 13 by measuring off-specular light scattering. The technique employs a focused light beam 10 that illuminates the area of the specimen surface which is scratched or otherwise altered by a stylus 5 pressed to this surface with a determined force (load). The stylus is slid along this surface with a determined speed and for a determined distance. In a preferred embodiment, the specimen is mounted on a turntable 4, and the stylus and the optical elements are stationary. The light scattering intensity is measured using a light detector 7 continuously or quasi-continuously and data is evaluated using a computer 9.

24 Claims, 2 Drawing Sheets

APPARATUS AND METHOD FOR SCRATCH WEAR TESTING OF THIN FILMS

The application claims benefit of provisional application Ser. No. 60/038,979 filed Feb. 26, 1997.

FIELD OF THE INVENTION

The present invention generally relates to methods and apparatus for wear testing a specimen. More particularly, this invention relates to tribological testing and to methods and apparatus for detecting surface features of a specimen using light scattering.

BACKGROUND OF THE INVENTION

Hard thin films have become pervasive in advanced technology. Numerous industry groups in the US and the global economy will benefit from the availability of a reliable tool with high sensitivity for testing of wear of thin films. Specific industry groups that will benefit from improved methods and equipment for wear characterization include automotive, aircraft and other transportation industries, the electronics and metals manufacturing industry as well as the sector producing machinery for the chemical, food and other process industries. A relatively new area of coating applications that will also benefit is biomedical components. Improved methods for evaluating wear encompass economic benefits that relate to extending the lifetime of machinery and bio-systems, to making engines and devices more efficient, to conserving scarce material resources, to saving energy, and to improving safety.

A number of new superhard materials in the form of thin surface films (coatings) are being developed and produced. Dynamic mechanical characterization, and wear testing in particular, is necessary to assess the quality of such coatings both during development and fabrication of numerous products. In their recent review article on microtribology entitled "Recent Progress in Microtribology" and published in *Wear*, Vol. 200, pg. 296, (1996), Kaneko et al. describe the ultimate goal of microtribology namely, "to create practical zero-wear devices with very small mass and very light load". The authors concede that "we have very little of the knowledge needed for microtribology" and more data must be obtained.

Currently, standard ASTM (and VAMAS) tests are used for wear testing at the macroscopic scale. Nanoindentation measurements and Atomic Force Microscopy (AFM) are available for testing of mechanical properties of such films at the microscopic scale. Macroscopic testing relies on weight and/or height loss measurement. Both macroscopic and microscopic methods use profilometry of wear marks. The macroscopic methods of wear testing are not adequate, however, to provide meaningful test results for superhard thin films. Also, wear testing at the microscopic scale is both expensive and cumbersome.

The difficulty in film characterization using macroscopic methods arises from two primary factors: (1) the hard film material is often deposited on a less hard substrate, and (2) film thicknesses are commonly very small. As a result, such films are not well supported against a highly localized force such as that of a stylus or pin. Coating failure may often only be detected as a change in the friction force. The critical load, which is the load at which the film is scratched off, decreases with decreasing film thickness. Dynamic multi-pass tests which allow repeated passage of the same area have revealed that in practice, failure may occur at forces that are less than one-third of the critical load.

For these reasons, standard macroscopic approaches for tribological coating evaluation, such as the Pin-on-Disk test (ASTM G 99-95a, Annual Book of ASTM Standards, Vol. 03.02, 1997), are not appropriate since these lack the necessary sensitivity for the measurements which are required. The standard tests use detection methods that include height and weight loss evaluations, wear track profilometry, ball area measurements, and friction force measurements. Of these detection methods, only friction force measurement qualifies as a dynamic test. Taken alone, however, it is quite insufficient to describe coating quality. No direct relationship has been established between changes in friction force and wear quality. The height and weight measurements are also not well suited for extremely thin superhard films deposited on less hard substrate materials. Changes in height observed as indentations may be related to compression of the substrate and not to film wear and changes in weight may be very small and difficult to detect when extremely thin films are removed during testing. Methods for hardness testing of very thin films using displacement versus force diagrams have been developed but hardness is not always predictive for wear properties of superhard coatings. These films often contain multiple solid phases and the combination of phases of different hardness can significantly reduce the wear resistance.

Nanoindentation methods have been developed in the last fifteen years. See, for example, J. B. Pethica, "Microhardness Tests with Penetration Depths Less than Ion Implanted Layer Thickness", in *Ion Implantation into Metals*, Pergamon Press, Oxford, 1982, p. 147. In such methods, displacement of a stylus is continuously recorded as the applied load gradually increases and decreases. Further development of these methods has proceeded toward controlling ever decreasing loads and increasing the displacement sensitivity. Today, loads as low as 100 nN can be applied and penetration depths as small as 1 nm can be detected using either capacitance displacement sensors or optical fiber displacement sensors.

While this approach is very useful for hardness measurement, it does not provide information related to surface wear. Most nanoindenters provide for no motion of the specimen and thus yield no wear information. If motion of the specimen is allowed, measurement of the scratch produced by the stylus is performed by cross-sectional profiling. Continuous wear testing is also not feasible using this method.

The wear testing procedure using AFM involves the use of the AFM stylus for causing wear of the specimen. The wear, if any, is periodically tested by obtaining micrographs of the area influenced by the stylus. Continuous or quasi-continuous testing is not feasible. Another weakness of this method as applied to superhard materials is that the stylus is subject to wear during the test and thus subsequent AFM micrographs are subject to changes not only due to changes in the specimen (wear) but also due to changes in the measuring device.

Both AFM and nanoindenter instruments are well developed and are commercially available from a number of manufacturers. These instruments are quite expensive because of their highly technical and complex design. The complexity results from measuring very small mechanical displacements of a stylus, wherefore the instrument must be extremely well insulated from vibration. A broader industrial application of nanoindenter and AFM instruments is hindered not only by the expense and complexity of these instruments but also by the complexity of the information obtained. Neither of these techniques is mentioned in the context of wear testing in the recent text on tribology by K. Holmberg and A. Matthews entitled "Coatings Tribology", which was published by Elsevier, Amsterdam, 1994.

It has been established that high contact pressure, low speed, and a large number of passes are necessary to obtain statistically significant results in scratch-load testing. See, for example, S. Bennett and A. Matthews, "Multifunction Scratch Tester", *Surface and Coatings Technology*, Vol. 75, p. 869 (1995). These requirements are very difficult to implement. In the case of AFM and nanoindenters, the achievement of statistically significant results would require making many scratches and going back to analyze maps of each of them. The underlying problem is that in these methods one obtains too much information about the detailed shapes of scratches. This information is excessive in the sense that it is not necessary for establishing the presence of wear. However, it may be useful information for other research purposes.

Although there is interest in obtaining information about the wear in a continuous fashion, neither the macroscopic nor the microscopic methods are adequate to provide such data. The ASTM G 99-95a Standard expressly warns against using continuous wear depth data collection using position-sensing gages because of the errors associated with such measurement. This warning applies both to the use of machine vision devices and interferometers to obtain continuous wear test data.

Light scattering measurement has not been previously used in the area of wear testing. The light scattering technique for surface roughness measurement was developed more than 20 years ago. The variation of the measurement of off-specular light scattering with the collection of the off-specular light using a hemispherical mirror is called total integrated scattering (TIS) technique and henceforth will be referred to with this acronym. The measurement of surface features using TIS on small surface areas has been demonstrated to allow surface roughness measurements with a sensitivity of 1 nm rms or better, as set forth in U.S. Pat. No. 4,954,722 and the article "Scanning Scattering Microscope for Surface Microtopography and Defect Imaging", Vol. 14, *Journal of Vacuum Science and Technology B*, pg. 2417 (1996), by J. Lorincik et al.

None of the prior art techniques discussed above are well suited for easy and reliable wear testing of films and particularly very hard thin films. The disadvantages of the prior art are overcome by the present invention. Improved methods and apparatus are hereinafter disclosed which are relatively simple and may be easily, economically, and reliably operated to test the wear of various materials.

SUMMARY OF THE INVENTION

The present invention involves both a method and an apparatus in which a stylus is pressed to and is moving along the surface to be tested for wear (hereafter to be referred to as the specimen). Off-specular scattering of a fine focused light beam from the thus evolving wear mark is detected, and measurement of the scattered light intensity and the changes thereof are used to evaluate the wear of the specimen. In this method, measurement of light scattering is used for the detection of surface modification in the process of and combined with dynamic scratch testing. The major parts of the tester are the stylus with the loading and motion mechanisms, the light source including the focusing optics, and the scattered light detection device including the computer data acquisition. The tester is preferably furnished with automation and climate control.

The stylus (a pointed hard tip, pin, or needle) can be a diamond, sapphire, or other material that is sufficiently wear resistant to be used in wear testing of hard materials, including thin films. The shape of the tip of the stylus may be spherical, pyramidal, or conical, among others. Assuming a spherical tip shape with radius r, the size of the wear mark is largely determined by the radius r and, for best results, r should be between 10 $\mu$m and 100 $\mu$m. The motion and loading mechanism may be somewhat similar to a turntable with a nearly balanced handle. The specimen is placed on the turntable and as it turns, the path of the stylus is a circle on the specimen's surface. The weight on the balanced handle is adjustable to provide calibrated load values to the stylus. The speed of the turntable movement is adjustable for the desired velocities used in wear testing.

The light source should be a nearly point or parallel source. An inexpensive He-Ne laser ($\lambda \approx 632.8$ nm) is preferable, although neither a coherent nor a polarized light source is necessary. A UV source and optics would increase the expense significantly but would provide increased sensitivity by up to a factor of two. The off-specularly scattered light may be detected either after collection using a hemispherical or other suitable mirror, or a small area detector may be used. The latter solution is simpler but it yields much less sensitivity. The detection of the light may be accomplished using light sensitive semiconductor diodes providing an electrical signal. Comparison of changes in the off-specularly scattered and specularly reflected light is not essential but this comparison may be used for filtering out spurious effects such as inadvertent changes in the light source intensity. If the specularly reflected light is not used, then it may be simply excluded from the measurement by using a light trap.

The inadequacy of the prior art methods for characterization and wear testing of superhard and thin films deposited on less hard substrates was the primary motivation for the development of this invention. The methods and apparatus described herein may be used for measuring wear under circumstances of quasi-continuous wear testing of superhard thin films deposited on less hard substrates. The provision of such a device is an objective of the present invention. The detection of wear using light scattering yields data that is directly related to wear and is obtained in real time as the wear occurs. Moreover, since measurements are being taken continually, a wealth of data is collected and achievement of statistical significance is not a problem.

The invention described herein relies on light scattering techniques using a focused light beam but does not involve microscopy or production of micrographs as disclosed in U.S. Pat. No. 4,954,722. A general limitation of the light scattering technique is saturation of the signal at large roughness values. Recent research has been in extending the range of application of the TIS technique to larger measures of roughness, i.e. greater than 0.1 wavelength, that can be evaluated using new mathematical approaches that replace first order perturbation theory. See, M. Bjuggren et al., "Quality Assessment of Engineering Surfaces by Infrared Scattering", *Proc. of SPIE*, Vol. 2536, pg. 327, (1995).

Various techniques and hardware accessories may be used to enhance the testing capabilities of this method. The signal-to-noise ratio of the measurement can be greatly improved when phase sensitive detection (lock-in detection) is used. To this end, a light chopper may be included in the light source. Spurious light may be excluded by housing the entire instrument under a non-transparent enclosure. The same enclosure may be utilized for providing climate controlled environment for the testing. If desired, the instrument may be built such that the testing is carried out in vacuum.

The surface of the specimen may be lubricated. However, one must carry out separate tests in order to establish whether the lubricant's optical properties change as a result of the testing. If the lubricant's optical properties do change, test results may become misleading.

The technique of this invention may be extended for the detection of friction and adhesion failure. Such extensions would make the instrument based on the present invention extremely useful in a wide area of mechanical testing of hard materials.

In this method, traditional wear detection methods, such as visual observation and trace profilometry, may be replaced with a highly sensitive and a quasi-continuous method which yields results in real time. An additional advantage of this method is the significant decrease of the force applied to the stylus that causes the wear. In order to avoid undue interference of the substrate properties with the tribological properties of a hard thin film under evaluation, the force applied to the stylus must be significantly smaller than in the standard (ASTM or VAMAS) tests. When applying small forces to hard specimens using prior art techniques, wear tests may not be carried out in a reasonable time. Detection methods are radically improved according to the present invention by the in-line monitoring of the changes in surface roughness using light scattering in off-specular direction. This method yields the following advantages: (1) Light scattering allows measurement of very small differences in surface roughness (of the order of 1 nm); thus, very small changes in topography related to wear can be detected. (2) The test need not be of a predetermined duration but the tester may be automated to notify testing personnel about the status, or failure, of the specimen. (3) The light scattering method is simple, inexpensive and easy to automate.

In contrast with the nanoindentation and AFM techniques, the measurements carried out with the present technique are those of changes in topography in the wake of a stylus rather than of movements of a stylus. Since light scattering is much less sensitive to the specimen vibration than the detection of position, it is not necessary to incorporate similar degree of vibration isolation as the nanoindenter and the AFM require. This makes the present technique much less expensive and much simpler.

These and further objects, features, and advantages of the present invention will become apparent from the following detailed description, wherein reference is made to the figures in the accompanying drawings.

DETAILED DESCRIPTION OF PREFERRED EMBODIMENTS

Figure 1:
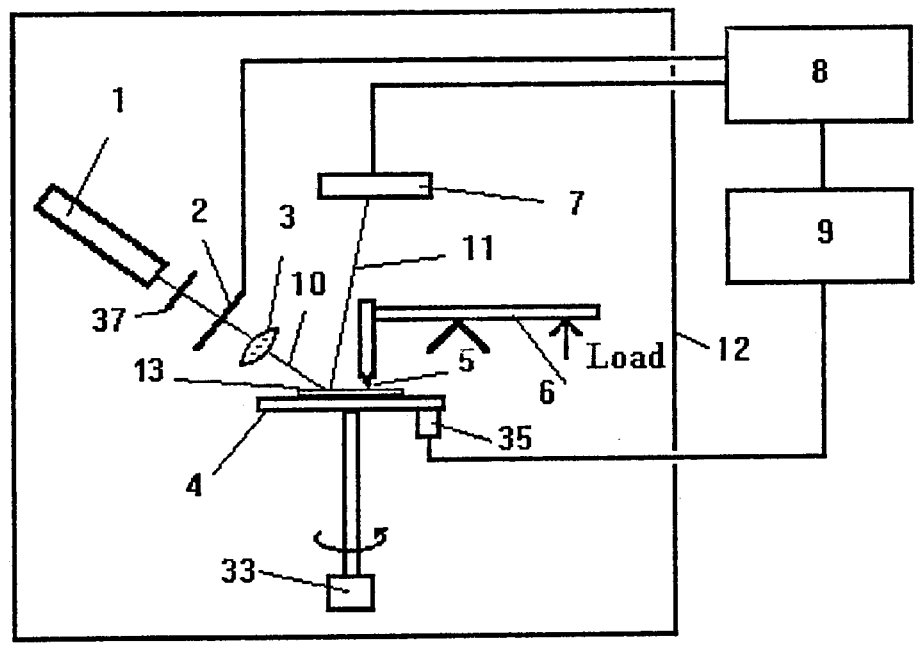
FIG. 1 is a schematic representation of the major components of one embodiment of a light scattering wear tester according to the present invention for testing flat specimens.

With reference to FIG. 1, the light scattering wear tester has a light source 1 directing a beam of light 10 onto the surface of specimen 13. The light on its way toward the specimen is passed through a chopper 2 and a focusing optics 3 which provides a light spot of the size of about 10 μm on the surface of the specimen 13.

The specimen 13 is mounted on the turntable 4. The stylus 5 with a load determined by the loading mechanism 6 is pushed against the specimen while the turntable 4 is in motion. The force on the stylus 5 causes wear of the specimen 13. The light beam 10 is directed at the circular track that is in the wake of the stylus 5. This substantially linear track is created during the test as a result of the process of wear. The detector 7 detects the off-specular scattered light 11 that originates from the illuminated spot on the track. The output of the detector 7 is processed by the phase sensitive lock-in amplifier 8 which receives a signal from the light chopper 2. The data are collected, stored and processed by the computer 9. The computer 9 also receives information about the position of the turntable 4. Essential parts of the system are enclosed in a shield 12 that protects from spurious light. This shield 12 may also serve as an enclosure for climate control and/or as a vacuum envelope.

The light source 1 can be an arc or an incandescent lamp which preferably is one that imitates a point light source; it may also be any similar light source or a laser. Since the intensity of the off-specularly scattered light is a function of the wavelength λ of the light, it is preferable to use a filter 37 or a monochromatic light source (such as a laser). The use of monochromatic light decreases measurement noise and, if the light is collected by a hemispherical mirror (TIS technique, not shown in FIG. 1), it also allows quantitative measurement of the surface roughness. In the TIS technique, the rms surface roughness $R_q$ can be calculated from λ and the intensities of the scattered and specularly reflected light, $I$ and $I_o$, respectively, as $$R_q = \frac{\lambda}{4\pi}\sqrt{I/I_o} \qquad \text{Equation 1}$$

In the case of relatively high roughnesses, filters may also be used in order to reduce the light intensity and prevent saturation of the light detector. Other optical elements, such as a beam expander, aperture plate, beam splitter, and additional light detectors may be included in the actual optical design. A separate light detector may be used for monitoring the intensity of the specularly reflected light. This is desirable in order to assure that the changes in the off-specular light intensity are not caused by changes in the light source. In a well designed instrument, the computer will register the $I/I_o$ ratio as the result of the light scattering measurement.

The turntable 4 may move with a wide variety of speeds and is preferably powered by an electric motor 33. The turntable 4 may be programmed to turn back-and-forth, i.e. to turn in one direction a certain number of times and then in the reverse direction for a certain number of times. The advantage of the back-and-forth movement is that the wear of the surface is realized while the stylus 5 is moving in two opposite directions with respect to the specimen 13.

In a different arrangement, the turntable 4 may be replaced with a table that moves straight back-and-forth in a direction perpendicular to the axis of the turntable 4. Other essential features and components of the wear tester may be the same as for the embodiment shown in FIG. 1.

The loading mechanism 6 may be essentially a slightly unbalanced lever. The force applied may result from an appropriately selected weight, from a spring, from an electromagnetic or a piezoelectric actuator, among others. In a different design, especially if using a piezoelectric actuator, the lever may be omitted and the force may be applied directly to the stylus 5.

The detector 7 may be a light-sensitive semiconductor device that may be integrated with a preamplifier. An amplifier 8 is desirable to provide adequate signal levels for the data recording device 9. The data recording is best accomplished by a suitably equipped and programmed computer 9.

To assure detection with a high signal-to-noise ratio, phase sensitive detection may be employed. This may be accomplished by using a light chopper 2 and a lock-in amplifier 8. The chopper 2 may be used to create an intermittent incoming light beam with a light passing frequency typically in the range of a few hundred Hz. The signal is measured using lock-in techniques. Using this technique combined with TIS, surface roughness measurements with a sensitivity of 1 nanometer rms or better may be achieved.

To detect changes in surface topography from a stylus 5 moving along the surface, the sensitivity of the light scattering technique is fully utilized only if the light beam is focused on the area that is subject to change. Focusing on the trace area increases the sensitivity of the measurement. This is due to the reduction in background signal generated by the uninfluenced surface. This feature of the wear tester makes the detection process fast. A positioning aid in the form of a microscope or telescope (not shown in FIG. 1) may be employed to ensure the correct positioning of the light spot on the specimen 13 with respect to the track of the stylus 5.

The light spot size may be chosen according to the known dimensions of the stylus and the specimen. For coated materials, one may assume that the depth of the wear mark will be no larger than the film thickness, t. In the case of hemispherical stylus of radius r>>t, the resulting wear mark will have a width $\tau \approx 2\sqrt{rt}$ or less. For example, if r=10 $\mu$m and t=100 nm, then $\tau \approx 2$ $\mu$m. In the case of a pyramidal or conical stylus, the width of the wear mark may be comparable to the width of the stylus at a distance of t from its tip. In any case, the width of the wear mark may be estimated before the test and measures may be taken to appropriately focus the light.

For the previously noted optimum stylus sizes (10–100 $\mu$m) and for a range of wear depth sizes of 10–1000 nm, $\tau$ ranges from 0.6 $\mu$m to 20 $\mu$m using the above equation. However, larger styli may be used and deeper wear may occur in special cases. As a practical matter, an upper limit on the wear mark size would likely be no larger than 200 $\mu$m. Thus the focused light beam spot generally should be no more than 200 $\mu$m, although in most cases much smaller spot sizes would be preferred since the light spot width (which generally would be the light spot mean diameter) with respect to the generally linear track should preferably approximate the width of the wear mark. Thus optimal light spot sizes in most cases should be less than 50 $\mu$m, and typically less than 20 $\mu$m.

Using the light scattering wear tester, measurement may be carried out continuously, i.e. wear data may be taken continuously during the wear process rather than in separate measurements at predetermined intervals of time. Alternatively, quasi-continuous (intermittent) measurements may be carried out on a certain area of the specimen 13. Such areas may be referred to as wear spots, i.e. a wear spot is a distinct area of the specimen 13 that is investigated for wear. For this, the computer control is utilized by triggering measurement cycles synchronized with the rotation of the turntable 4 in such a way that data at each turn are collected when the same wear spot crosses the light beam 10. Such an event will be referred to henceforth as a pass. A sensor 35 may be provided for sensing the position of the test specimen relative to the stylus, i.e., the sensor 35 may output a signal to the computer 9 each time one rotation or pass of the turntable 4 occurs, or if desired each time the turntable 4 rotates a selected amount such as 90 degrees. Collecting data from the same wear spot at different passes enables the user to evaluate the development of the wear process. There also may be more than one wear spot monitored in each turn. A similar procedure of evaluating wear spots is also feasible for testing cylindrical and spherical specimens.

The specimen 13 to be tested may have an areal distribution of surface roughness. In such cases, the wear tester should be used in the quasi-continuous mode in order to avoid receiving misleading or chaotic data. In other words, the light scattering measurement is performed intermittently at each pass, i.e. when the same wear spot passes through the light beam 10. A similar procedure is feasible for cylindrical and spherical specimens.

The specimen 13 to be tested may be transparent or translucent. If such is the case, scattered light from scattering centers in the bulk of the specimen 13 may interfere with the measurement. Likewise, if a film is being tested, scattered light from scattering centers at the film-substrate interface may interfere with the measurement. However, the light scattered from these scattering centers will remain constant and independent of the wear situation. Again, the light scattering measurement is used intermittently when the same wear spot passes through the light beam. A similar procedure is feasible for cylindrical and spherical specimens.

The light scattering signal may be stored in the memory of the computer 9. Comparison of data obtained during different passes on the same surface area may be made automatically using computer software. The software may be used to determine whether the surface change that has accumulated through a wear process is sufficient and the test may be concluded.

Figure 2:
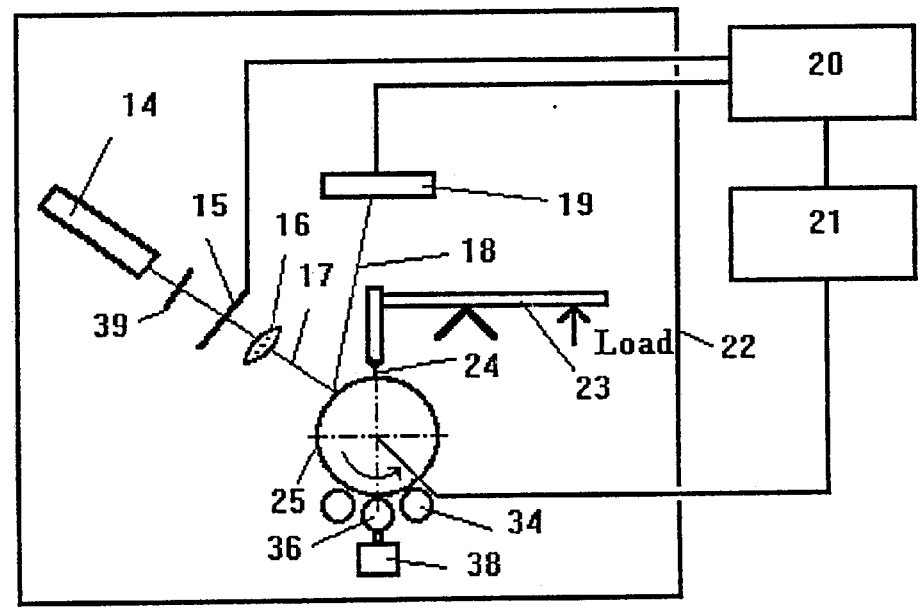
FIG. 2 is a schematic representation of the major components of a light scattering wear tester for testing specimens with rotational symmetry.

The arrangement shown in FIG. 1 is useful for testing specimens where the surface containing the track is substantially planar or flat. The method of this invention may also be used for specimens of other shapes. With reference to FIG. 2, in the case of cylindrical, spherical, or other specimens that exhibit symmetry about at least one axis, the preferred test method is one in which the specimen 25 is turned around its axis. For this, a turning and specimen holder mechanism may be provided that ensures that the specimen 25 turns around its axis in a direction essentially perpendicular to the loading force of the stylus 24 so that the wear mark of the stylus 24 is a circle around the perimeter of the specimen 25. A simplistic test specimen holder and turning mechanism as shown in FIG. 2 comprises a plurality of idler rollers 34, drive roller 36, and drive motor 38. The other elements of the wear tester are the same as in the case of flat specimens, as shown in FIG. 1.

Figure 3:
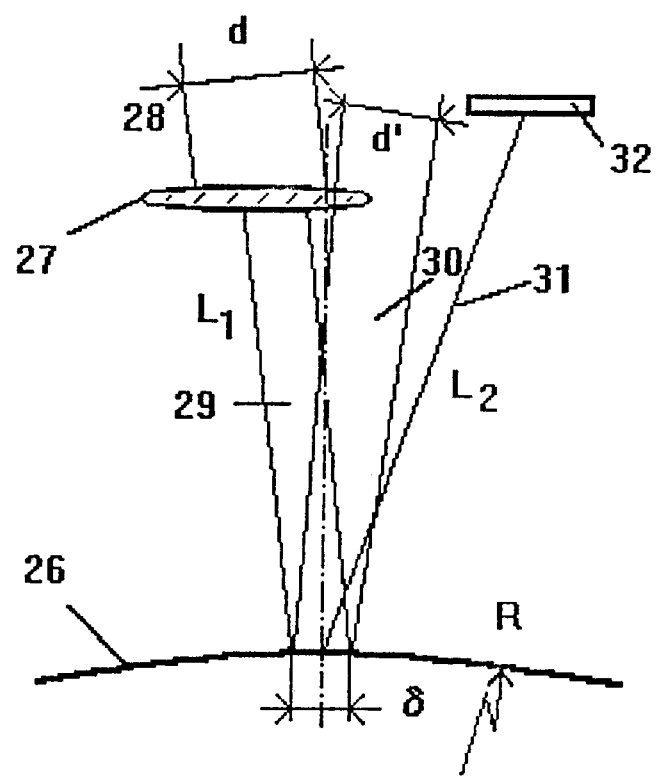
FIG. 3 is a schematic representation of the effect of the curvature of a reflecting surface on the size of the specularly reflected light beam.

With reference to FIG. 3, in the case of a cylindrical or spherical surface 26 with radius R, specularly reflected light will be excluded from detection if reflected light is not collected within the area characterized by diameter d' around the specular direction. The primary light beam 28 of diameter d is focused on the specimen surface 26. The focusing element (lens) 27 is at a focusing distance $L_1$ from the specimen. The focused light beam 29 reaches the spot diameter $\delta$ at the point of reflection. The diameter of the specularly reflected light beam 30 reaches the value d' at the distance $L_2$ from the specimen 26 to the detector 32. The detector 32 is outside the specularly reflected light beam 30 so that it collects only the off-specularly scattered light 31.

The diameter d' of the reflected light beam 30 is related to the diameter d of the original light beam 28 with the relationship $$d' \approx \frac{L_2}{L_1}d + 2L_2\frac{\delta}{R} \qquad \text{Equation 2}$$

The above relationship is a good approximation if d<<L$_1$ and δ<<R. Under realistic circumstances these conditions are easily fulfilled. For example, if d=1 mm, L$_1$=100 mm, δ=10 μm and R=10 mm, then L$_1$=100d and R=1000δ. If L$_2$ is the same as L$_1$ (100 mm) then d'≈1.2 mm. Hence, there is no significant limitation in collecting the off-specularly scattered light from curved specimen surfaces as long as the radius of the curvature is large compared to the light spot size. This is an additional benefit of using focused light for the wear testing.

For the preferred embodiments disclosed herein, the light source, stylus, and detector are fixed and the test specimen is moved relative to the stylus to form the wear track. For very large test specimens, these fixed components could be mounted on a movable member, such as a rail, so that the test specimen remained stationary during the test. Also, an x-y table could be provided instead of the turntable, and the specimen position sensor 35 could then provide as input to the computer the position of the specimen (or the x-y table) relative to the stylus. If desired, a rectangular shaped track could thus be formed on the test specimen, and the number of passes the stylus makes along the track could then be recorded as previously described. Alternatively, the x-y table could move the stylus in a straight linear path, with the stylus retracing the linear path in a back and forth motion. In the preferred embodiment, the surface being tested is perpendicular to the loading force of the stylus.

The foregoing disclosure and description of the invention are illustrative and explanatory, and various changes in the components as well as in the method of conducting the test may be made within the scope of the invention, which is defined by the claims.

What is claimed is:

1. An apparatus for testing the surface wear characteristics of a test specimen, comprising:
    a stylus for moving against the surface of the test specimen and wearing the test specimen surface along a track;
    a light source for directing a light beam as a spot having a mean diameter less than 200 microns on the track formed on the test specimen;
    a detector for detecting off-specular scattered light originating from the track in response to a light source; and
    a data recorder responsive to the detector for recording surface wear characteristics of the test specimen.

2. The apparatus as defined in claim 1, further comprising:
    focusing optics for focusing the light from the light source on the test specimen.

3. The apparatus as defined in claim 1, further comprising:
    a shield for enclosing the test specimen and the detector and for protecting the detector from spurious light.

4. The apparatus as defined in claim 1, wherein the data recorder includes a computer for collecting and processing data from the detector.

5. The apparatus as defined in claim 1, further comprising:
    a loading mechanism for selectively adjusting the force of the stylus pressed against the test specimen.

6. The apparatus as defined in claim 1, wherein the light source directs a monochromatic light beam on the test specimen.

7. The apparatus as defined in claim 1, further comprising:
    a filter for passing light from the light source as a monochromatic light beam on the test specimen.

8. The apparatus as defined in claim 1, further comprising:
    the test specimen has a surface to be tested which lies substantially within a single plane;
    a turntable for rotating the test specimen to form a substantially circular track on the test specimen; and
    a motor for powering rotation of the turntable.

9. The apparatus as defined in claim 1, further comprising:
    the test specimen has a curved surface with an axis of symmetry to be tested;
    a test specimen holder for rotating the test specimen about the axis of symmetry such that the stylus presses against the curved surface of the test specimen to form a substantially circular track on the test specimen; and
    a motor for powering rotation of the specimen.

10. The apparatus as defined in claim 1, further comprising:
    a position sensor for sensing the position of the test specimen relative to the stylus; and
    the data recorder receives signal from the position sensor.

11. The apparatus as defined in claim 1, further comprising:
    a light chopper for creating an intermittent incoming light beam having a selected light passing frequency on the test specimen.

12. The apparatus as defined in claim 11, further comprising:
    an amplifier for receiving signals from both the detector and the light chopper to enhance sensitivity.

13. An apparatus for testing the surface wear characteristics of a test specimen, comprising:
    a stylus for moving against the surface of the test specimen and wearing the test specimen surface along a track;
    a light source for directing a light beam on the track formed on the test specimen;
    a light chopper for creating an intermittent incoming light beam having a selected light passing frequency;
    focusing optics for focusing the light from a light source as a spot on the test specimen;
    a detector for detecting off-specular scattered light originating from the track in response to the light beam originating from a light source;
    an amplifier for receiving signals from both the detector and the light chopper to enhance sensitivity; and
    a computer for collecting and processing data from the amplifier.

14. The apparatus as defined in claim 13, further comprising:
    a loading mechanism for selectively adjusting the force of the stylus pressed against the test specimen.

15. The apparatus as defined in claim 13, further comprising:
    a sensor for sensing the position of the test specimen relative to the stylus; and
    the computer receives signal from the specimen position sensor.

16. The apparatus as defined in claim 13, further comprising:
    a shield for enclosing the light source, the light chopper, the focusing optics, the test specimen, the stylus, and the detector and for protecting the detector from spurious light.

17. A method of testing the surface wear characteristics of a test specimen, comprising:

pressing a stylus against the surface of the test specimen;

moving the stylus relative to the surface of the test specimen and wearing the test specimen surface along a track;

creating a light beam that is monochromatic;

directing the light beam such that it illuminates a spot on the wear track formed on the test specimen;

detecting off-specular scattered light originating from the track in response to the light source; and recording data from the detector.

18. The method as defined in claim 17, further comprising:

enclosing a stylus, a light source, and a detector to protect the detector from spurious light.

19. The method as defined in claim 17, further comprising:

focusing the light from a light source as a spot on the test specimen having a mean diameter of less than 200 microns.

20. The method is defined in claim 17, further comprising:

sensing the position of the test specimen relative to the stylus; and collecting and processing data from the detector as a function of the sensed position of the test specimen.

21. The method as defined in claim 17, further comprising:

selectively adjusting the force of the stylus pressed against the test specimen.

22. The method as defined in claim 17, further comprising:

creating an intermittent incoming light beam having a selected light passing frequency illuminating the test specimen.

23. The method as defined in claim 17, further comprising:

rotating the test specimen to form a substantially circular track on the test specimen; and powering a motor to rotate the test specimen.

24. The method as defined in claim 17, further comprising:

sensing the position of the test specimen relative to the stylus; and collecting and processing data from the detector as a function of the sensed position of the test specimen.

* * * * *